(12) United States Patent
Rheinwald et al.

(10) Patent No.: US 8,114,068 B2
(45) Date of Patent: Feb. 14, 2012

(54) LIGHT GUIDE

(75) Inventors: Markus Rheinwald, Kaufering (DE); Benno Rückle, Pocking (DE)

(73) Assignee: Dornier MedTech Laser GmbH, Wessling (DE)

( * ) Notice: Subject to any disclaimer, the term of this patent is extended or adjusted under 35 U.S.C. 154(b) by 553 days.

(21) Appl. No.: 11/874,057

(22) Filed: Oct. 17, 2007

(65) Prior Publication Data

US 2008/0158629 A1  Jul. 3, 2008

(30) Foreign Application Priority Data

Oct. 17, 2006  (EP) .................................... 06021726

(51) Int. Cl.
*A61B 18/18* (2006.01)
*A61H 33/00* (2006.01)
*A61N 1/30* (2006.01)
*G02B 5/32* (2006.01)

(52) U.S. Cl. ................ 606/15; 606/16; 607/89; 604/20; 359/15; 385/37

(58) Field of Classification Search ............ 359/15, 359/34, 569; 385/37; 606/11, 15, 16; 607/89; 604/20

See application file for complete search history.

(56) References Cited

U.S. PATENT DOCUMENTS

| | | | |
|---|---|---|---|
| 4,261,345 A | 4/1981 | Yamaguchi | |
| 4,519,390 A | 5/1985 | Horne | |
| 4,592,353 A | 6/1986 | Daikuzono | |
| 4,669,819 A | 6/1987 | Hengst et al. | |
| 4,693,244 A | 9/1987 | Daikuzono | |
| 4,722,337 A | 2/1988 | Losch et al. | |
| 4,736,743 A | 4/1988 | Daikuzono | |
| 4,781,185 A | 11/1988 | Kauphusman et al. | |
| 4,822,997 A | 4/1989 | Fuller et al. | |
| 4,852,567 A | 8/1989 | Sinofsky | |
| 4,907,588 A | 3/1990 | Burston | |
| 5,061,032 A * | 10/1991 | Meltz et al. | 385/37 |
| 5,071,222 A | 12/1991 | Laakmann et al. | |
| 5,098,427 A * | 3/1992 | Hessel et al. | 606/11 |
| 5,112,328 A | 5/1992 | Taboada et al. | |
| 5,130,533 A | 7/1992 | Ruf | |
| 5,133,035 A * | 7/1992 | Hicks | 385/117 |
| 5,139,494 A | 8/1992 | Freiberg | |
| 5,139,495 A | 8/1992 | Daikuzono | |
| 5,154,708 A | 10/1992 | Long et al. | |
| 5,190,535 A | 3/1993 | Daikuzono | |

(Continued)

FOREIGN PATENT DOCUMENTS

CA  2066963  11/1992

(Continued)

OTHER PUBLICATIONS

Abou-Jawde, R. et al., An Overview of Targeted Treatments in Cancer, *Clinical Therapeutics*, vol./Iss: 25 (8), pp. 2121-2137, 2003.

(Continued)

*Primary Examiner* — Audrey Y Chang

(74) *Attorney, Agent, or Firm* — King & Spalding

(57) ABSTRACT

The invention relates to a light guide with at least one photorefractive area, wherein a volume hologram is formed in the photorefractive area in such a way that light coupled into the light guide can be decoupled by the volume hologram at a predetermined angle and/or with a predetermined focus.

19 Claims, 3 Drawing Sheets

U.S. PATENT DOCUMENTS

Figure 1:
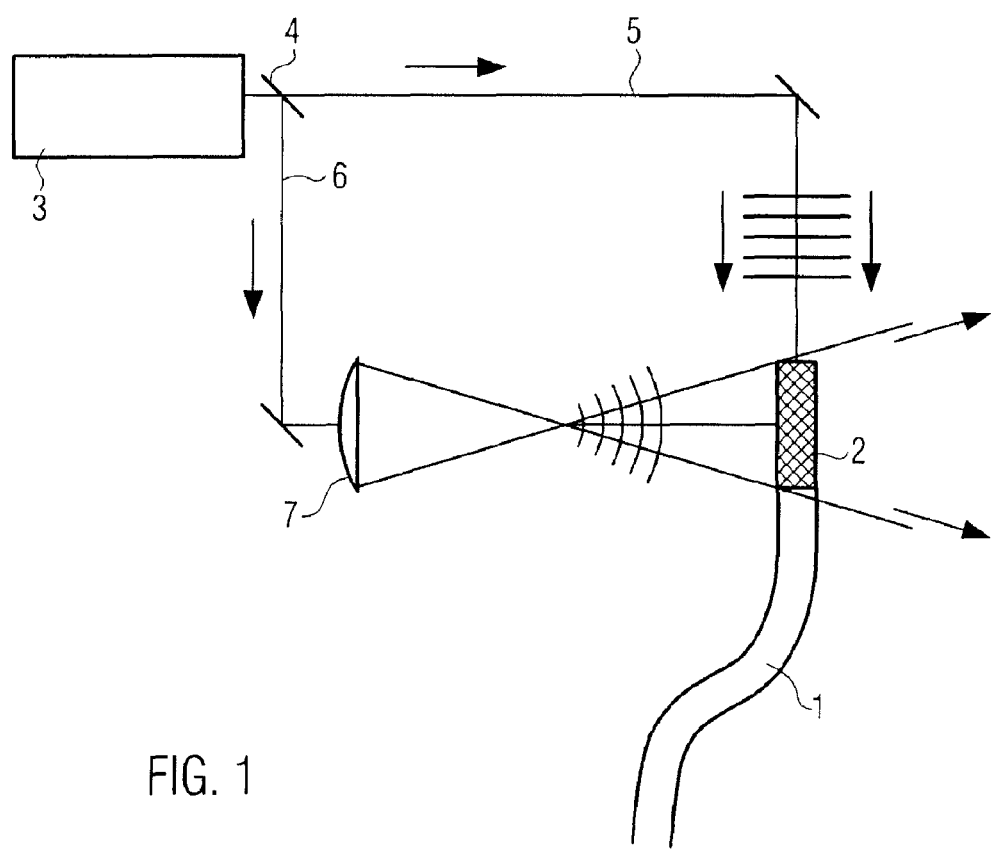

| | | |
|---|---|---|
| 5,300,066 A | 4/1994 | Manoukian et al. |
| 5,360,447 A | 11/1994 | Koop |
| 5,409,537 A | 4/1995 | Poullos et al. |
| 5,415,655 A | 5/1995 | Fuller et al. |
| 5,416,878 A | 5/1995 | Bruce |
| 5,454,808 A | 10/1995 | Koop et al. |
| 5,490,849 A | 2/1996 | Smith |
| 5,520,681 A | 5/1996 | Fuller et al. |
| 5,535,399 A | 7/1996 | Blitz et al. |
| 5,540,676 A | 7/1996 | Freiberg |
| 5,607,420 A | 3/1997 | Schuman |
| 5,681,307 A | 10/1997 | McMahan |
| 5,688,263 A | 11/1997 | Hauptmann et al. |
| 5,693,043 A | 12/1997 | Kittrell et al. |
| 5,738,679 A | 4/1998 | Daikuzono |
| 5,742,718 A | 4/1998 | Harman et al. |
| 5,784,512 A * | 7/1998 | Hensen ............. 385/61 |
| 5,841,562 A | 11/1998 | Rangwala et al. |
| 5,860,972 A | 1/1999 | Hoang |
| 5,867,618 A * | 2/1999 | Ito et al. ............ 385/37 |
| 5,872,618 A | 2/1999 | Nagayama et al. |
| 5,908,417 A | 6/1999 | Miller et al. |
| 5,951,543 A | 9/1999 | Brauer |
| 5,957,915 A | 9/1999 | Trost |
| 5,971,755 A | 10/1999 | Liebermann et al. |
| 6,022,345 A | 2/2000 | Miller et al. |
| 6,086,366 A | 7/2000 | Mueller et al. |
| 6,092,722 A | 7/2000 | Heinrichs et al. |
| 6,162,218 A | 12/2000 | Elbrecht et al. |
| 6,193,711 B1 | 2/2001 | Connors et al. |
| 6,270,491 B1 | 8/2001 | Toth et al. |
| 6,273,885 B1 | 8/2001 | Koop et al. |
| 6,377,591 B1 | 4/2002 | Hollister et al. |
| 6,398,778 B1 | 6/2002 | Gu et al. |
| 6,423,055 B1 | 7/2002 | Farr et al. |
| 6,477,426 B1 | 11/2002 | Fenn et al. |
| 6,567,582 B1 | 5/2003 | Rizoiu et al. |
| 6,699,239 B1 | 3/2004 | Stiller et al. |
| 6,829,427 B1 | 12/2004 | Becker |
| 7,006,749 B2 | 2/2006 | Illich et al. |
| 7,020,361 B2 | 3/2006 | Thiele et al. |
| 7,114,855 B2 | 10/2006 | Wittrisch |
| 7,215,864 B1 | 5/2007 | Qian et al. |
| 7,503,701 B2 | 3/2009 | Hiereth et al. |
| 2002/0073082 A1 | 6/2002 | Duvillier et al. |
| 2002/0081080 A1 | 6/2002 | Balle-Petersen et al. |
| 2002/0183811 A1 | 12/2002 | Irwin |
| 2004/0037498 A1 | 2/2004 | Thiele et al. |
| 2004/0114879 A1 | 6/2004 | Thiele et al. |
| 2005/0013551 A1 | 1/2005 | Hung |
| 2005/0105859 A1 | 5/2005 | Gerhard |
| 2006/0122281 A1 | 6/2006 | Escandon et al. |
| 2007/0179485 A1 | 8/2007 | Yeik et al. |
| 2008/0033341 A1 | 2/2008 | Grad |
| 2008/0071333 A1 | 3/2008 | Hayes et al. |

FOREIGN PATENT DOCUMENTS

| | | |
|---|---|---|
| CA | 2093297 | 11/1993 |
| DE | 8416748.3 | 8/1984 |
| DE | 9013085.5 * | 1/1991 |
| DE | G 9013085.5 | 1/1991 |
| DE | 4013455 | 10/1991 |
| DE | 4025851 | 2/1992 |
| DE | 4216254 | 8/1994 |
| DE | 4229566 | 8/1996 |
| DE | 19534590 | 3/1997 |
| DE | 19629646 | 9/1998 |
| DE | 19729978 * | 1/1999 |
| DE | 69229128 | 2/2000 |
| DE | 10009004 | 10/2001 |
| DE | 10106297 | 1/2002 |
| EP | 0325836 | 8/1989 |
| EP | 0325836 A2 | 8/1989 |
| EP | 404968 | 1/1991 |
| EP | 0404968 A1 | 1/1991 |
| EP | 433464 | 6/1991 |
| EP | 0433464 B1 | 6/1991 |
| EP | 473987 | 3/1992 |
| EP | 0473987 A1 | 3/1992 |
| EP | 0495605 | 7/1992 |
| EP | 0495605 A2 | 7/1992 |
| EP | 514258 | 11/1992 |
| EP | 0514258 A1 | 11/1992 |
| EP | 0292622 * | 12/1996 |
| EP | 0292622 B1 | 12/1996 |
| EP | 0820787 | 1/1998 |
| EP | 1527748 | 5/2005 |
| JP | 03033808 | 2/1991 |
| JP | 04-226404 | 8/1992 |
| JP | 2002162524 | 6/2002 |
| JP | 2002162524 A | 6/2002 |
| WO | WO 93/21841 | 11/1993 |
| WO | WO 93/21841 A1 | 11/1993 |
| WO | WO 98/47032 | 10/1998 |
| WO | WO 9847032 A | 10/1998 |
| WO | WO 99/15237 | 4/1999 |
| WO | WO 99/15237 A1 | 4/1999 |
| WO | WO 2004/000099 | 12/2003 |
| WO | WO 2004/012805 | 2/2004 |
| WO | WO 2007/104836 | 9/2007 |

OTHER PUBLICATIONS

Bronchud, M. et al., Selecting the Right Target for Cancer Therapy, *Principles of Molecular Oncology*, pp. 3-27, 2000.

D'Amico, A., Radiation and Hormonal Therapy for Locally Advanced and Clinically Localized Prostate Cancer, *Urology*, vol./Iss: 58 (Suppl. 2A), pp. 78-82, 2001.

Douwes, F. et al., Neoadjuvant Hormone Ablation before HIFU Treatment of Localized Prostate Cancer, *Alternative and Complementary Therapies*, vol./Iss: 18 (Suppl. 1), pp. A43, Nov. 2004.

Hua, L. et al., High Intensity Focused Ultrasound Combined with Endocrine Therapy in Treating Prostate Cancer, *National Journal of Andrology*, vol./Iss: 11(3), Pages: Abstract, Mar. 2005.

Hurwitz, M. et al., Feasibility and Patient Tolerance of a Novel Transrectal Ultrasound Hyperthermia System for Treatment of Prostate Cancer, *International Journal of Hyperthermia*, vol./Iss: 17(1), pp. 31-37, 2001.

Lein, M. et al., Laser-Induced Hyperthermia in Rat Prostate Cancer: Role of Site of Tumor Implantation, *Urology*, vol./Iss: 56, pp. 167-172, 2000.

Marberger, M. et al., Energy-Based Ablative Therapy of Prostate Cancer: High Intensity Focused Ultrasound and Cryoablation, *Current Opinion in Urology*, vol./Iss: 17, pp. 194-199, 2007.

Strohmaier, W. et al., Influence of Transrectal Hyperthermia on Prostate-Specific Antigen in Prostatic Cancer and Benign Prostatic Hyperplasia, *Urologia Internationalis*, vol./Iss: 51(1) abstract, pp. 28-31, 1993.

Thueroff, S. et al., Neoadjuvant Hormone Ablation before HIFU Treatment of Localized Prostate Cancer, *Journal of Endourology*, vol./Iss: 18(Suppl 1), pp. A43, Nov. 2004.

Trachtenberg, J. et al., Microwave Thermoablation for Localized Prostate Cancer after Failed Radiation Therapy: Role of Neoadjuvant Hormonal Therapy, *Molecular Urology*, vol./Iss: 3(3), pp. 247-251, 1999.

* cited by examiner

LIGHT GUIDE

The invention relates to a light guide, particularly for laser applicators.

Laser applicators facilitate, for example, the treatment of biological tissue with laser radiation in the medical area. For example, in laser-induced thermotherapy (LITT), with the help of a catheter a glass fibre for guiding the laser radiation is placed directly on or in a tissue area that is to be treated. The laser light radiated through the applicator and into the surrounding tissue is absorbed and leads to a local temperature increase, which produces coagulative and hyperthermic effects. This in return results in immediate or delayed tissue necrosis.

Optical fibres or optical waveguide fibres such as are used for laser applicators normally consist of mineral glass or organic glass (plastic). A core is surrounded by a cladding and a coating, whereby the cladding has an optical refractive index that is lower than that of the core, so that there is total reflection at the boundary layer between the core and cladding, and therefore guidance of the radiation in the core.

The fibre core is, for example, suitably abraded at certain points for the release or decoupling of the laser radiation from the fibre, so that homogeneous radiation is achieved in these areas. In this way, the laser radiation is given off by the applicator divergently, so that the energy density is greatest at the catheter surface and falls off strongly as the distance to the applicator increases. As a result, the laser radiation has the strongest effect in the area close to the applicator, which brings with it the risk of overheating or burning at the applicator surface.

In the state of the art, an azimuthal asymmetry is achieved by applying a one-sided reflective coating on the catheter. As an alternative to this, catheters are used that have movable mirrors arranged in their interior, whereby these mirrors can be moved during a movement of the catheter so that the laser beams hit the same spot in a chronological order. With this arrangement, an azimuthal asymmetry can be achieved by restricting the motion range of a movable mirror. During the movement of the catheter or the movable mirror, however, thermal energy is lost due to heat conduction, so that the efficacy of this type of treatment is impaired. Furthermore, the mirror configuration is complex and subject to failure.

In light of this state of the art, it is an object of the present invention to provide a light guide that is easy to manufacture and reliable, particularly for laser applications in, for example, the medical area, whereby with this light guide, coupled radiation can be decoupled and shaped in the required and efficient manner. At the same time, local overheating at the catheter surface or at the fibre surface should be avoided.

This object is achieved by means of a light guide in accordance with Patent Claim 1.

According to the invention, a light guide with at least one photorefractive area is provided, whereby a volume hologram is formed in the photorefractive area in such a way that coupled light in the light guide can be decoupled by the volume hologram at a predetermined angle and/or with a predetermined focus.

It has surprisingly turned out that the use of such volume holograms reliably allows the decoupling of light in the desired manner. Such a light guide does not have a complicated configuration, and is therefore not subject to failure. Depending on the desired application, it is consequently possible to provide a corresponding light guide with which decoupling of the light can be achieved at a certain angle and/or at a certain focus.

Photorefractive means that the refractive index continually changes under the light influence. A photorefractive material is consequently photosensitive. A volume hologram, in particular a volume phase hologram, can be produced in a simple manner by using photorefractive materials. A volume hologram is a holographic grid that has not-too-insignificant expansion in three dimensions, which means also particularly in the direction of the propagation of the light beams.

The photorefractive area can be provided at an end of the light guide. This allows light to be decoupled, particularly at points that are hard to access.

The photorefractive area can comprise a material that is different from the material in the rest of the light guide. This makes it possible to select the materials appropriately for the light guide, depending on the area. Consequently, for example, a material with optic characteristics that are particularly advantageous for the volume hologram can be selected for the photorefractive area and a material that, firstly, has the characteristics needed for the light guiding characteristic and, where necessary, a high level of flexibility, can be selected for the rest of the light guide.

The photorefractive area can be formed in a section of the light guide that is connected to the rest of the light guide in such a way that it can be detached, either without destruction or with destruction. The section with the photorefractive area can, in particular, be fused with the rest of the light guide.

Alternatively, the photorefractive area can be provided along the entire length of the light guide. In particular, this makes it possible to form one or more volume holograms at any desired points on the light guide.

The photorefractive area can be formed in the core of the light guide. In particular, the core of the entire light guide can comprise a photorefractive material.

The photorefractive area can comprise a very wide range of inorganic and organic materials. In particular, it can comprise a germanium-doped glass. The photorefractive area can additionally or alternatively have a doping of hydrogen, particularly in the form of a hydrogen-doped glass. Further suitable materials are cited, for example, in E. Mecher, "*Erhöhung der Sensitivität photorefraktiver holographischer Speichermedien auf Basis von amorphen organischen Materialien*" (*Increase in the sensitivity of photorefractive holographic storage media on the basis of amorphous organic materials*"), Dissertation, LMU (Ludwig Maximilian University) Munich, 2001.

The light guide can be formed as optical fibres. Optical fibres, which consequently comprise a photorefractive area with a volume hologram, are particularly suitable for use in, for example, medicine for minimally invasive procedures. Such optical fibres furthermore also simplify the processing of inorganic materials, particularly in hollow spaces.

In the case of the previously described light guides, the predetermined focus can comprise a point focus, line focus, ring focus or triangle focus. Furthermore, the predetermined focus can take the form of a combination of a point, line, ring and/or triangle. The focus can consequently be adjusted to the type of desired use of the light guide.

In particular, the predetermined focus can comprise a ring focus with the optical axis of the light guide as the axis of symmetry. To be understood as the optical axis of a light guide is the axis along which the light is guided in the light guide. In an optical fibre, the fibre itself forms the axis of symmetry.

The light guide can be developed to guide laser radiation, particularly in the infrared range. Infrared laser radiation is particularly suitable for laser-induced thermotherapy.

The invention furthermore provides a laser applicator for the treatment of biological tissue with laser radiation, comprising one of the previously described light guides. Furthermore, a laser applicator for the processing of inorganic materials comprising one of the previously described light guides is also provided.

In these cases, the photorefractive area can particularly be provided at the distal end of the laser applicator.

The invention furthermore provides a method for producing a light guide, particularly as previously described, with the steps:

Provision of a light guide with a photorefractive area, and
Development of a volume hologram in the photorefractive area, so that light coupled into the light guide can be decoupled by the volume hologram at a predetermined angle and/or with a predetermined focus.

The provision can comprise the steps:

Provision of a light guide element and an element comprising the photorefractive area, and
Connection of the element to the light guide element, whereby the volume hologram is formed before or after the connecting.

Particularly in the case of an optical fibre, the provision of an element with the photorefractive area can comprise provision of a further light guide element, particularly with the photorefractive fibre core.

Connecting the light guide element and the photorefractive element can comprise a fusing. Other forms of connection, particularly also for destruction-free, detachable connecting, are likewise possible, however.

The development of a volume hologram can comprise irradiation with two partial beams of UV laser light, whereby one partial beam is modified in accordance with the volume hologram to be developed.

Figure 2:
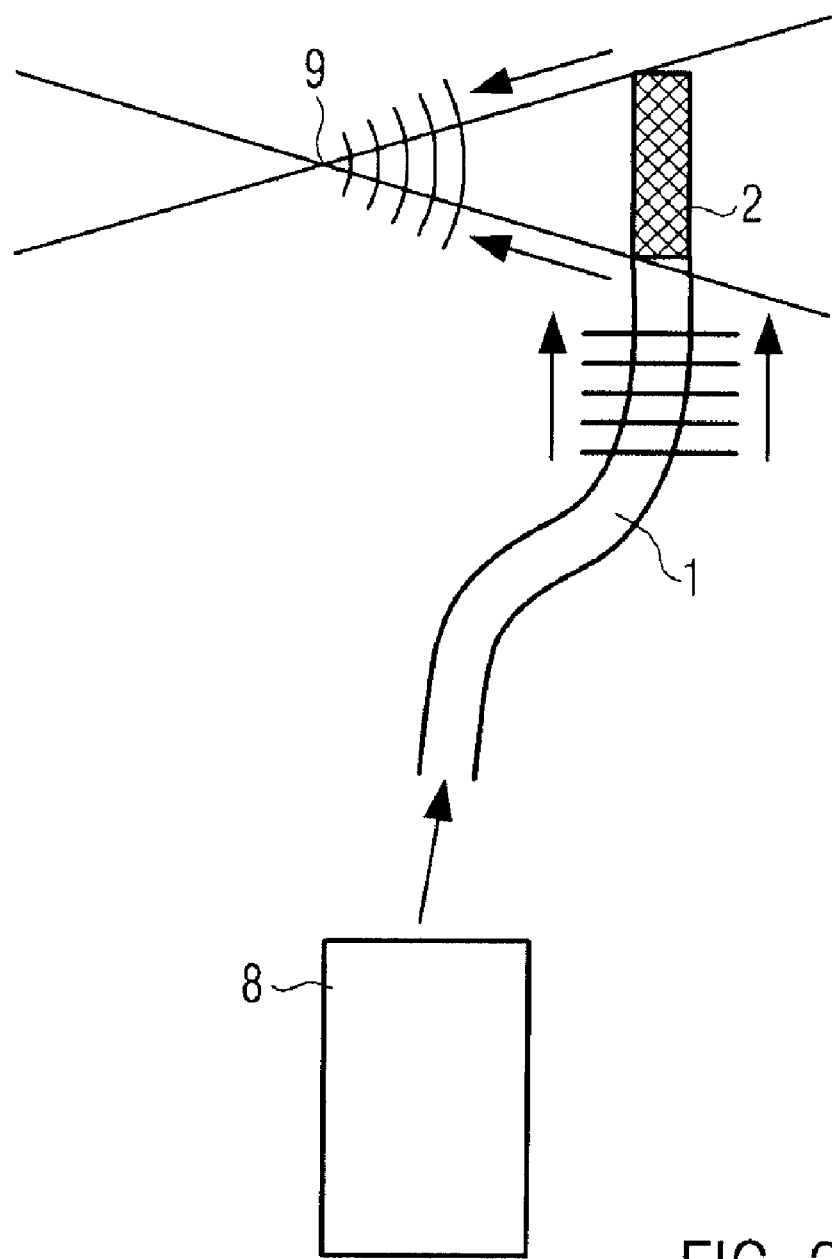
Figure 3:
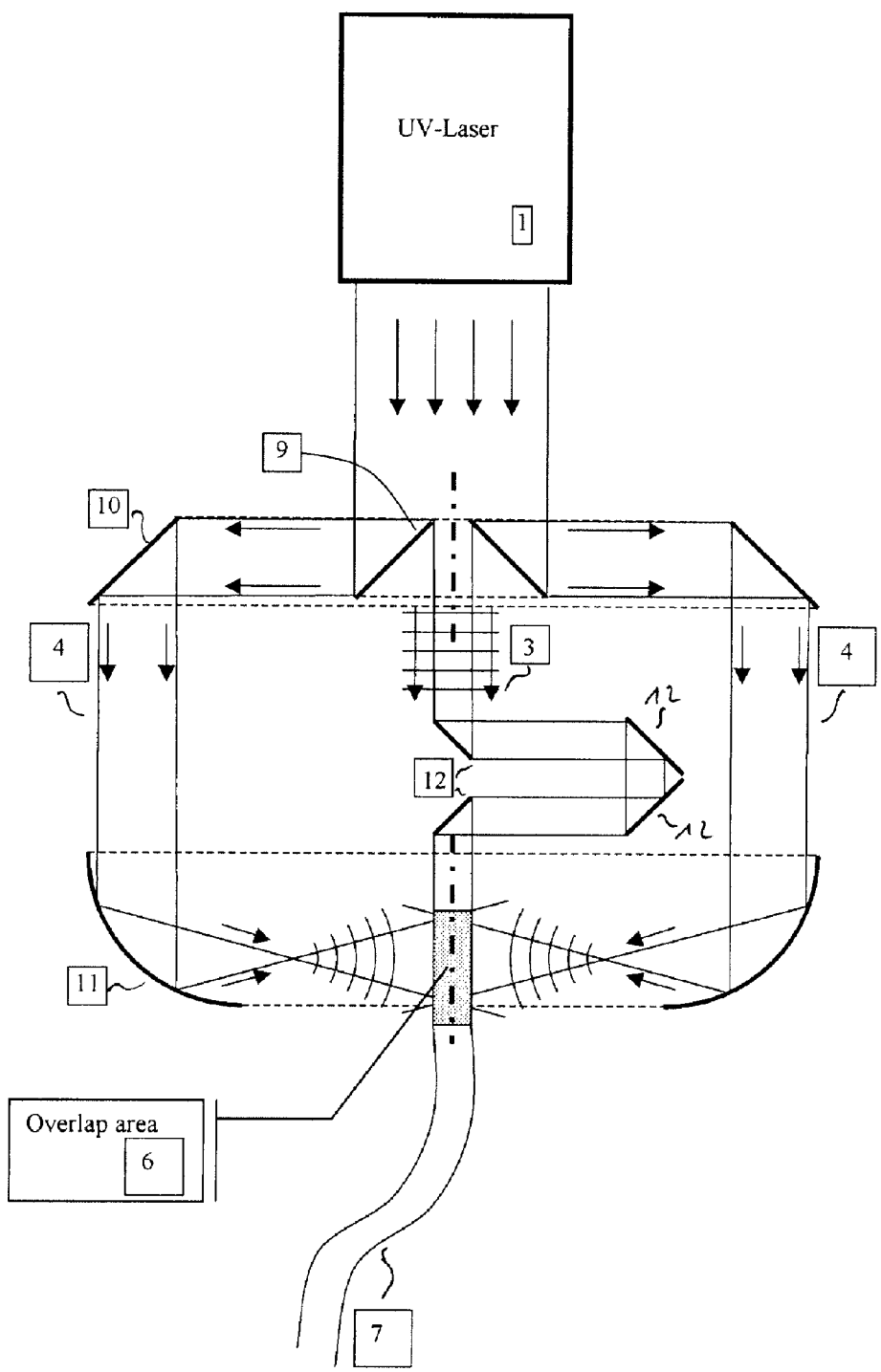

Further characteristics and advantages of the invention are described in the following on the basis of the figures. The figures illustrate:

FIG. 1 schematically, a method for producing a light guide with a volume hologram, FIG. 2 schematically, the application of an example of a light guide with a volume hologram, FIG. 3 schematically, a method for producing a light guide with a volume hologram.

FIG. 1 illustrates the production of a volume hologram at the distal end of an optical fibre by way of example. In this process, an optical fibre 1 is provided with a section 2 with a photorefractive area.

For example, the optical fibre can be a glass fibre with a fibre core made of glass. It is photosensitized at its distal end, section 2. This section with the photorefractive area can, for example, be a piece of optical fibre with a fibre core made of germanium-doped glass. The fibre core can furthermore be doped with hydrogen. This section is then connected to the rest of the optical fibre, for example, by fusing.

A volume hologram is produced in the photorefractive area by means of irradiation with two UV partial laser beams. Provided for this purpose is a UV light source (3) that emits a laser beam in the UV range.

Possible for use as the UV light source are, for example, pulsed excimer lasers with wavelengths of 193 nm or 248 nm, a frequency-doubled argon ion laser (500 mW, cw) with a wavelength of 244 nm or a frequency-quadrupled Nd:YVO4 laser (100 mW, cw) with a wavelength of 266 nm.

With the help of a beam splitter 4, the laser beam is split into two partial beam paths (5) and (6). The one partial beam 5 is coupled into the optical fibre with an approximately level wave front on the distal end.

The other partial beam 6 is modified according to the volume hologram to be developed or according to the desired decoupling characteristic by means of lens and/or mirrors. In the example shown, the second partial beam 6 is focused at a point some predetermined distance from the optical fibre by means of a lens 7. A point focus is consequently produced. The laser beam subsequently falls onto the photorefractive area 2.

In the photorefractive area of section 2, the two partial beams 5 and 6 interfere and produce a volume phase hologram. Both partial beam paths must have the same optical path length from the laser 3 to the overlap area.

If the entire fibre core is photorefractive, this writing of the volume hologram into the section 2 can basically take place both after and during the pulling process of the optical fibre. When a light guide element without photorefractive fibre core and an additional fibre element with photorefractive core are used, both connected to each other, the writing can fundamentally accordingly be carried out before or after the connecting. Preferably it takes place after the connecting, however, because the two light guide elements have then been fixed in place in the relative arrangement.

In the production of a volume hologram that is, during a subsequent use of the optical fibre, intended to decouple the light at a different angle or with a different focus than that shown in the figure, the second partial beam 6 must be modified accordingly. Instead of a point focus, a line focus, ring focus or triangle focus, for example, can consequently be produced. Furthermore, overlap of a number of these foci is also possible.

FIG. 2 schematically illustrates the operation of a light guide on the distal end of which is formed a volume hologram. Shown is a light guide 1 that has resulted from the method in accordance with FIG. 1, said light guide 1 having a section 2 with a photorefractive area in which a volume hologram is formed for a point focus.

In the application use, the beam of a laser 8 is coupled into the fibre 1 proximally, consequently reaching the area of the volume hologram from the direction opposite to the direction of insertion of the holographic grid according to FIG. 1.

Depending on the desired application, an Nd:YAG laser with a wavelength of 1064 nm or a diode laser with a wavelength between 800 and 1000 nm, for example, can be used as the laser 8. Suitable laser powers can, for example, be between 5 and 100 W.

When the coupled beam reaches the dispersion area located at the distal end, it is bent by the volume hologram in such a way that the beam path of the second partial beam 6 of FIG. 1 is obtained in the reverse direction. In this way, the coupled light is decoupled from the optical fibre in the section of the photorefractive area and has a point focus 9. The efficiency of the beam deformation in the volume hologram here depends particularly on the coherence characteristics of the laser 8 used.

FIG. 3 schematically shows an example of an optical configuration for producing a volume hologram that can produce a ring-shaped focus during the reconstruction. The beam of an ultraviolet laser 1 is split into two partial beams 3 and 4 by the mirror 9. This case requires that the laser beam of laser 1 has sufficiently good spatial coherence. The mirror 9 has the shape of a cone with a central hole. The radiation is deflected to the side by 90 degrees, rotationally symmetrically, by the mirror 9. The likewise rotationally symmetrical mirror 10 diverts the laser radiation by 90 degrees again, so that it again runs parallel to the optical axis.

The laser radiation is focused by the rotationally symmetrical concave mirror 11 in a ring shape 90 degrees towards the optical fibre. After the passage through the focus, the radiation is again divergent and finally reaches the overlap area 6 at the distal end of the fibre 7.

The partial beam 3 that runs through the central hole of the mirror 9 is directed via an arrangement of 4 plane mirrors, which are identified with the number 12. This mirror arrangement 12 serves the optical path length compensation. The path lengths of the partial beams 3 and 4 are adjusted to the same length in this way. The partial beam 3 then meets the practically flat wave fronts at the overlap area 6 at the distal fibre end. There the partial beams 3 and 4 interfere and produce a volume hologram.

Light guides of this kind, particularly optical fibres, can be used in a very wide range of areas. In medical applications, for example, an optical fibre can be introduced into a natural body opening or can be brought to the treatment point with the help of an endoscope or catheter. Tissue in areas that are difficult to reach can be ablated or coagulated by the laser radiation that is decoupled at any selected angle and with any selected focus. Consequently, a light guide of this type is particularly suited for interstitial treatments, gastroenterology, urology or angioplasty.

In addition to medical applications, however, it is also possible to process inorganic materials, for example, with such a light guide. Because light guides can be particularly easily guided into hollow spaces, an ablation and/or hardening of inner cylinder walls in motors, for example, can be performed with such a light guide.

The invention claimed is:

1. A medical laser applicator, comprising:
   a light guide comprising at least one photorefractive area comprising a volume hologram, the volume hologram being configured to decouple infrared light that has been coupled into the light guide, the decoupled infrared light having at least one of a predetermined angle and a predetermined focus,
   wherein the at least one photorefractive area is disposed at one end of the light guide and a remainder of the light guide is a non-photorefractive area,
   wherein the at least one photorefractive area comprises a material that is different from a material of the remainder of the light guide, and
   wherein the medical laser applicator is configured to treat biological tissue with laser radiation emitted from the light guide.

2. The medical laser applicator according to claim 1, wherein the photorefractive area comprises a germanium-doped glass.

3. The medical laser applicator according to claim 1, wherein the photorefractive area comprises a hydrogen-doped glass.

4. The medical laser applicator according to claim 1, wherein the light guide is formed as an optical fiber.

5. The medical laser applicator according to claim 1, wherein the predetermined focus comprises a point focus.

6. The medical laser applicator according to claim 1, wherein the predetermined focus comprises a line focus.

7. The medical laser applicator according to claim 1, wherein the predetermined focus comprises a triangle focus.

8. The medical laser applicator according to claim 1, wherein the predetermined focus comprises at least one of a point, a line, a ring, and a triangle.

9. The medical laser applicator according to claim 1, wherein the predetermined focus comprises a ring focus having an axis of symmetry along an optical axis of the light guide.

10. The medical laser applicator according to claim 1, wherein the light guide is configured to guide infrared laser radiation.

11. A method for treating biological tissue with laser radiation, comprising the steps of:
    providing a medical laser applicator comprising
       a light guide having a photorefractive area, the photorefractive area comprising a volume hologram configured to decouple infrared light that has been coupled into the light guide, the decoupled infrared light having at least one of a predetermined angle and a predetermined focus,
       wherein the at least one photorefractive area is disposed at one end of the light guide and a remainder of the light guide is a non-photorefractive area,
       wherein the at least one photorefractive area comprises a material that is different from a material of the remainder of the light guide; and
    medically treating biological tissue by applying the decoupled infrared light from the light guide to the biological tissue.

12. The method according to claim 11, wherein the step of providing the medical laser applicator comprises the steps of:
    providing a light guide element and a second element comprising the photorefractive area;
    connecting the second element to the light guide element; and
    creating the volume hologram in the photorefractive area,
    wherein the step of creating the volume hologram occurs before the connecting step or after the connecting step.

13. The method according to claim 12, wherein the step of connecting the second element to the light guide element comprises the step of fusing the second element to the light guide element.

14. The method according to claim 12, wherein the step of creating the volume hologram comprises the step of irradiating two partial beams of UV laser light, at least one of the partial beams being modified by at least one of a lens and a mirror based on at least one characteristic of the volume hologram being created.

15. The method according to claim 11, wherein the photorefractive area comprises a germanium-doped glass or a hydrogen-doped glass.

16. The method according to claim 11, wherein the light guide is formed as an optical fiber.

17. The method according to claim 11, wherein the predetermined focus comprises a point focus, a line focus, a triangle focus, or a ring focus.

18. The method according to claim 11, wherein the predetermined focus comprises a ring focus having an axis of symmetry along an optical axis of the light guide.

19. The method according to claim 11, wherein the light guide is configured to guide infrared laser radiation.

\* \* \* \* \*